United States Patent [19]

Brezinski

[11] 4,401,548

[45] Aug. 30, 1983

[54] REFERENCE ELECTRODE WITH INTERNAL DIFFUSION BARRIER

[75] Inventor: Donald P. Brezinski, Corning, N.Y.

[73] Assignee: Corning Glass Works, Corning, N.Y.

[21] Appl. No.: 233,993

[22] Filed: Feb. 12, 1981

[51] Int. Cl.³ .......................................... G01N 27/30
[52] U.S. Cl. ..................................... 204/435; 204/420
[58] Field of Search ..................................... 204/195 F

[56] References Cited

U.S. PATENT DOCUMENTS

| | | | |
|---|---|---|---|
| 3,264,205 | 8/1966 | Leonard et al. | 204/195 |
| 3,267,016 | 8/1966 | Arthur | 204/195 |
| 3,423,304 | 1/1969 | Leonard | 204/195 |
| 3,498,899 | 3/1970 | Kater et al. | 204/195 G |
| 3,528,903 | 1/1968 | Taylor | 204/195 |
| 3,530,056 | 9/1970 | Haddad | 204/195 |
| 3,676,319 | 7/1972 | Kirsten | 204/195 F |
| 3,843,506 | 10/1974 | Jerrold-Jones | 204/195 F |
| 3,915,829 | 10/1975 | Krebs | 204/195 |
| 4,002,547 | 1/1977 | Neti et al. | 204/195 F |
| 4,053,382 | 10/1977 | Maruyama et al. | 204/195 |
| 4,177,126 | 12/1979 | Imaki et al. | 204/195 F |
| 4,184,935 | 1/1980 | Schindler et al. | 204/195 |

FOREIGN PATENT DOCUMENTS 729575  5/1955  United Kingdom ............ 204/195 F

OTHER PUBLICATIONS

*Analytical Chemistry*, vol. 27, No. 3, Mar., 1955, pp. 472 & 473.

Primary Examiner—T. Tung
Attorney, Agent, or Firm—W. E. Maycock

[57] ABSTRACT

Improved reference electrode of the double junction type wherein the half-cell junction is characterized in that the mathematical quotient of its liquid flow rate divided by its ionic electrical conductance under defined test conditions is less than about 0.12 $ml \cdot hr^{-1} \cdot mho^{-1}$.

8 Claims, 3 Drawing Figures

REFERENCE ELECTRODE WITH INTERNAL DIFFUSION BARRIER

BACKGROUND OF THE INVENTION

The present invention is concerned with reference electrodes, and the reference electrode portion of combination electrodes, which are employed to provide the stable reference potentials required by a variety of electroanalytical techniques, such as ion-selective electrode measurements, controlled potential coulometry, polarography, and the like. More particularly, the present invention is concerned with what commonly are referred to in the art as double junction reference electrodes.

A reference electrode most frequently is used in conjunction with an ion-selective electrode, either separately or in combination, to measure the activity (which is a function of concentration) of a given ion in a sample solution. Consequently, the discussion which follows primarily relates to such use. It is to be understood, however, that such discussion is not intended to in any way limit the spirit or scope of the present invention.

The two electrodes, i.e., the reference electrode and the ion-selective electrode, both of which are immersed in the sample solution, typically are connected to a means for measuring the potential difference between the electrodes, e.g., an electrometer. The reference electrode provides a constant electromotive force or potential against which the potential of the ion-selective electrode is compared. The latter potential consists of a constant component from the electrochemical half-cell of the ion-selective electrode and a variable component which is the potential across the sensing membrane and which is dependent upon the activity (concentration) of the ion being measured. The variable component, then, is readily correlated with ion activity (concentration) by known means. To give accurate results, the potential of the reference electrode should not change with the composition of the sample.

The reference electrode is designed to be minimally sensitive to changes in the external, sample ionic environment. It consists of at least three components: (1) a half-cell electrode (typically a silver-silver chloride mixture), (2) a half-cell electrolyte (typically 4 M potassium chloride solution saturated with silver ions), and (3) a reference junction. The half-cell electrode and half-cell electrolyte constitute an electrochemical half-cell having a known, stable, constant electrical potential. Direct physical, and therefore electrical, contact between the half-cell electrolyte and the sample solution is established through the reference junction which usually consists of a porous ceramic plug, metal or asbestos fiber bundle, sintered plastic, or like means of achieving a fluid mechanical leak.

As used herein, the term "half-cell electrode" means the solid-phase, electron-conducting contact with the half-cell electrolyte, at which contact the half-cell oxidation-reduction reaction occurs which establishes the stable potential between the half-cell electrolyte and the contact.

A major disadvantage of conventional reference electrodes of the above-described type is that the same electrolyte is used to accomplish two unrelated tasks: (1) setting the potential of the electrochemical half-cell, and (2) establishing contact with the sample solution via the reference junction. Half-cell ions, such as $Ag^+$ in an Ag/AgCl electrode, $Hg^+$ in a calomel electrode, and $Tl^+$ in a thallium amalgam electrode, are also present at the reference junction where they may contaminate the measured solution and, in certain circumstances precipitate, clogging the junction.

For example, one of the major deficiencies of Ag/AgCl electrodes is the tendency of AgCl or other silver salts to precipitate within the junction, clogging it and interfering with free diffusion between the measured solution and internal electrolyte. Manifestations of a clogged reference junction include slow response, stirring-dependent potentials, and erroneous potentials at equilibrium.

Clogging increases response time by stopping the outward flow of junction electrolyte. In the absence of outward flow, the measured solution diffuses deep into the reference junction and temporarily serves as the junction electrolyte when the next solution is measured. The result may be a large diffusion potential which persists until the old sample is cleared from the junction by diffusion. With adequate outward flow, response time is minimized since the measured solution cannot penetrate deep into the junction and is flushed rapidly away during the next measurement.

Clogging by AgCl or other heavy metal salts may also cause non-ideal response in low ionic strength samples. This results in static error (due to the shift in potential upon entering the charged junction), stirring effects (due to shifts in static error with local changes in electrolyte concentration at the junction surface), and flow-dependent potentials (due to streaming potentials generated within the junction).

The tendency of the Ag/AgCl electrode to clog is particularly unfortunate, since it otherwise is an excellent electrode that offers high stability, ease of manufacture, low toxicity and extended temperature range.

AgCl tends to precipitate in the junction because AgCl is much more soluble in the usual 4 M KCl internal electrolyte than in the solutions in which the electrode is usually immersed. While the solubility of AgCl in pure water is very low, about $1.3 \times 10^{-5}$ M, the solubility of AgCl in 4 M KCl is about 500-fold higher, around $7 \times 10^{-3}$ M. This high solubility is attributable to the formation of negatively charged ionic complexes between $Ag^+$ and $Cl^-$ having the general form $Ag_nCl_{n+1}^-$. When AgCl-saturated 4 M KCl flows or diffuses into a more dilute solution, the $Cl^-$ concentration is reduced and the excess silver chloride is precipitated. Precipitation of silver salt is often evident as a darkening of the external surface of the reference junction element and is particularly noticeable on older ceramic junctions.

My experiments indicate that junctions of conventional Ag/AgCl electrodes clog very rapidly. Even a new electrode can lose most of its flow capability after less than 24 hours in solution.

Contamination of the measured solution by heavy metal ions in the junction electrolyte is another problem associated with conventional reference electrodes. While silver is not particularly poisonous, its presence could be a problem in certain applications, e.g., photographic and forensic chemistry. $Tl^+$ and $Hg^+$ ions are very poisonous, and $Hg^+$ has been observed to inhibit a variety of enzymatic reactions.

Metal salts cannot simply be omitted from the electrolyte of conventional reference electrodes since they are required to establish a stable electrode potential. Even if the metal salt is initially located only at the half-cell element, as in an AgCl-dipped silver wire, the salt will dissolve and quickly spread by diffusion and convection until the electrolyte is saturated. Deliberate confinement is required.

One approach to eliminating undesired ions in the junction electrolyte is to use a so-called "double junction electrode", in which separate compartments containing the reference-junction and half-cell electrolytes are connected by an internal liquid junction provided by, for example, a porous ceramic plug. Double junction electrodes are widely used in ion-selective electrode measurements where it is desirable to use a salt other than KCl as the junction electrolyte, but have not been generally used for the specific purpose of excluding heavy metal ions from the junction electrolyte. Nevertheless, they could be used for the latter purpose. However, conventional double junction electrodes have several related deficiencies. Double junction electrodes of current art have inner junctions of ceramic or other materials which are far too permeable to adequately inhibit flow under pressure without using thicknesses that needlessly increase the electrical impedance of the electrode. Stated differently, common junction materials are too permeable to yield barriers through which mixing is limited by ionic diffusion rather than liquid flow. In a typical double junction electrode, the inner half-cell compartment is refillable and the half-cell electrolyte flows under gravity through the inner junction into the junction electrolyte. This requires periodic refilling of the inner electrolyte and causes contamination of the external electrolyte. However, even if the inner compartment is sealed, mixing between inner and outer electrolytes can still occur as a consequence of diffusional interchange and also as a consequence of bulk flow through the inner junction due to pressure gradients brought about by thermal expansion or changes in ambient pressure.

In particular, inner junction materials of the current art are generally so permeable that, in sealed half-cell configurations, the mixing of half-cell and junction electrolytes caused by flow due to atmospheric pressure variations will far exceed the mixing caused by ionic inter-diffusion in the absence of flow. For example, the Corning double junction electrode (Cat. No. 476067, Corning Medical and Scientific Division, Corning Glass Works, Corning, N.Y.) uses a barely porous (1% void-volume) ceramic that was specifically developed for low flow. However, even with this ceramic, measurements of flow versus pressure indicated that solution exchange caused by average atmospheric fluctuations of $\pm 3$ cm Hg would be about ten-fold higher than exchange due to diffusion. Atmospheric fluctuations of $\pm 3$ cm Hg are equivalent to a steady head of about 1 cm in driving solution through the junction.

Thermal expansion and water vapor pressure at elevated temperatures (e.g., 90° C.) were observed to cause much higher internal pressures and rapid loss of half-cell electrolyte. This expulsion of electrolyte from the half-cell compartment was accompanied by electrolyte dehydration, causing an increase in ionic concentrations and, consequently, a drift in the electrode potential. Also, half-cell dehydration was found to cause thermal hysteresis by causing the KCl concentration to rise high enough to exceed saturation levels at lower temperatures.

Some double junction electrodes have half-cell compartments containing electrolyte gelled with thickening agents such as water-soluble organic polymers. Such gelling of the inner electrolyte helps cut down flow, but I have found gelling agents to be relatively ineffective in preventing flow over the wide range of temperatures and pressures to which electrodes may be subjected. Also, the thickeners commonly used (agar and sodium carboxymethylcellulose) are subject to bacterial, thermal, and chemical degradation, and may also cause clogging of the inner junction. Since these thickeners also generally bear electrically charged groups, such clogging may cause erratic and drifting electrode potentials if the junction electrolyte is low in ionic strength.

Finally, the role of junction resistance in preventing diffusional exchange of ions has not been appreciated in the prior art. I have found that the rate of diffusional exchange of solution species through a porous barrier is inversely proportional to the electrical resistance of the barrier when saturated with a test electrolyte, but is independent of the barrier's size, shape, or structural detail. Thus, the effectiveness of a diffusion barrier is completely characterized by its electrical resistance value, which must usually be appreciable to adequately retard diffusional mixing of electrolytes. (The resistance value of the barrier may be measured by saturating it with 4 M KCl electrolyte, applying a voltage to electrolyte solutions separated by the barrier, and determining the ratio of the voltage across the barrier to the resulting ionic current.) It is noteworthy that in many prior art reference electrodes which provide separate compartments for half-cell and junction electrolytes, the internal junctions have electrical resistance values which are far too low to prevent substantial diffusional exchange during periods of prolonged use or storage.

A final consideration in the performance of reference electrodes is that their impedance (electrical resistance) should be as small as possible, since, as discussed in my co-pending application Ser. No. 230,457, "Noise Suppressing Bypass for Reference Electrode", the electrical noise susceptibility of an electrometer circuit is in most cases directly proportional to the impedance of the reference electrode.

SUMMARY OF THE INVENTION

It is an object of this invention to provide an improved double junction reference electrode.

A more specific object of the present invention is to provide an improved double junction reference electrode including a microporous barrier positioned between the half-cell electrolyte and the junction electrolyte to more effectively prevent migration of undesired ions from the half-cell electrolyte to the junction electrolyte.

A still more specific object of the present invention is to provide an improved double junction reference electrode in which the internal barrier is such that the total rate of exchange between half-cell and junction electrolyte species is, within the limits of practical use, limited by diffusion rather than flow, so that the barrier resistance required to limit total exchange may be as small as possible.

Still another object of the present invention is to provide a reference electrode characterized by improved speed and accuracy of response, improved potential stability, and less thermal drift and hysteresis.

Other objects of the invention will be apparent to the skilled artisan from the detailed description of the invention, hereinbelow.

In accordance with the present invention, there is provided, in a double junction reference electrode comprising (a) a first housing containing an electrochemical half-cell being electrically connectable to an external measuring means and consisting essentially of a half-cell electrode and a half-cell electrolyte, (b) a second housing containing a junction electrolyte, (c) a half-cell junction allowing ionic conduction between said half-cell electrolyte and said junction electrolyte, and (d) a reference junction allowing ionic conduction between said junction electrolyte and an external sample to be measured, the improvement which comprises said half-cell junction comprising a microporous barrier material having a structure of sufficiently fine pore size such that exchange between half-cell and junction electrolytes is limited by diffusion, rather than by flow, characterized in that, when said half-cell junction is saturated with 4 M KCl, the mathematical quotient of the liquid flow rate through said half-cell junction at 1 cm Hg pressure divided by the ionic electrical conductance of said half-cell junction is less than about $0.12$ ml.hr$^{-1}$.mho$^{-1}$.

The use of a porous glass as a salt bridge is cited in the prior art, e.g., W. M. Carson et al., Anal. Chem., 27, 472 (1955). However, such prior use differs from the present invention in several significant and nonobvious aspects, as discussed below.

In the above reference, porous VYCOR ® glass was used as the reference junction of a single junction reference electrode to provide a salt bridge between the external solution to be measured and the half-cell electrolyte. In the present invention, a microporous barrier material which can be VYCOR ® glass is used as the inner junction of a double junction reference electrode and consequently does not come into direct contact with the sample solution. This difference in configuration allows much improved electrode performance, since the performance requirements of the inner and outer junctions are quite dissimilar and therefore benefit from separate optimization.

In particular, I have found that such microporous materials as porous VYCOR ® are poorly suited for use as external junctions. Because of their high porosity and negligible outward flow, such junctions allow deep inward diffusion of external or sample solution species which causes very slow electrode response. Also, junction space charge effects, clogging, and poor durability are problems likely to be encountered when microporous materials are used for the external or outer junction, as illustrated by the following examples:

(1) Junctions of porous VYCOR ® exhibit boundary potentials when immersed in solutions of very low ionic strength, because the high surface-to-volume ratio of the very small pores accentuates the effect of glass surface charge in excluding electrolyte ions of the same polarity.

(2) Microporous junctions are more easily clogged by adsorption of extraneous materials from the sample solution. For example, porous VYCOR ® has a high affinity for proteins and lipids in solution and, consequently, is readily clogged by them.

(3) Porous VYCOR ® has quite poor durability in highly alkaline and fluoride-containing solutions, precluding its use as an outer junction in such environments.

The utilization of porous VYCOR ® as an external or outer junction material has been extremely limited, possibly because of problems such as those cited above. These disadvantages are overcome in the present invention by exposing the microporous barrier material to an intermediary junction electrolyte, rather than directly to the solution to be measured. Since the same junction electrolytes typically are used for many successive measurements, thereby keeping the ionic composition within the microporous barrier material essentially constant, the response time of the inner junction is not response-limiting. Furthermore, junction electrolytes below about $10^{-2}$ in ionic strength rarely are used, so space charge effects at the inner junction are much less critical than at the outer junction where ionic strengths as low as $10^{-7}$ (e.g., distilled water) can be encountered. Additionally, junction electrolytes typically are inert salt solutions of essentially neutral pH, e.g., solutions of $NH_4SO_4$, KCl, and the like, so the inner junction is less subject to clogging by extraneous materials or chemical degradation.

Further aspects of the present invention also are not obvious from the prior art. For example, the deleterious effects of AgCl-clogging of the reference junction have not been adequately appreciated; consequently, the advantage of a Ag/AgCl reference electrode with a silver-free junction electrolyte was not apparent. More generally, the role of junction resistance in preventing ion diffusion is not understood in the prior art. In the above article citing the use of porous VYCOR ® as a salt bridge, the low electrical resistance of various bridge fabrications was cited as an advantage, whereas the severe leaching (diffusion) of salt from the porous glass was cited as a disadvantage. It is apparent from my work, however, that a low resistance and a low leaching rate are mutually incompatible objectives since junction resistance and diffusional transport are inversely related. As taught herein, a junction resistance which limits diffusional exchange to desired levels can be provided. While porous VYCOR ® saturated with 4 M KCl has a relatively low bulk resistivity, VYCOR ® barriers of the desired high resistance are obtained by the use of adequately long and thin junctions.

DETAILED DESCRIPTION OF THE INVENTION

Figure 1:
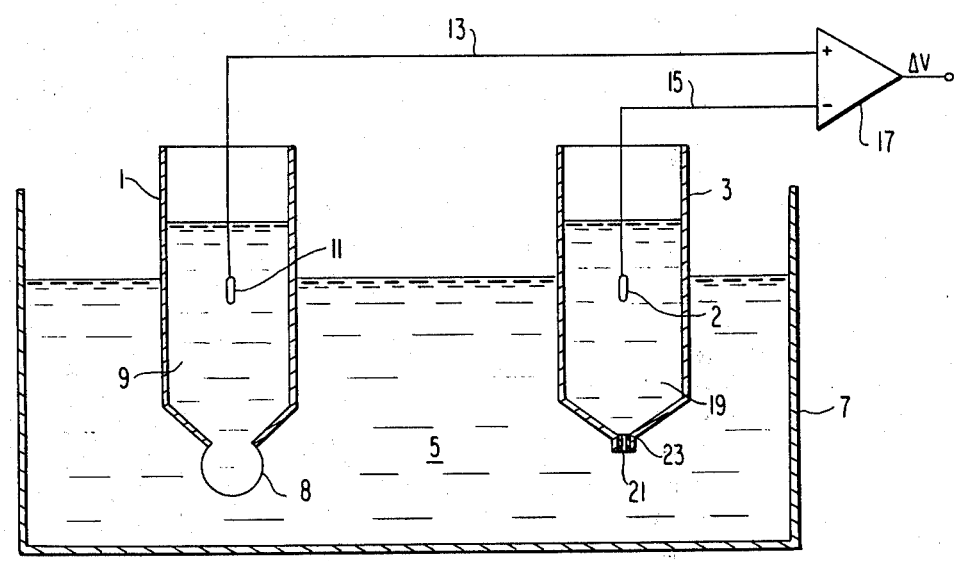
FIG. 1 of the Drawing is a schematic of a typical pH measurement system, illustrating the essential components thereof.

FIG. 1 depicts the essential elements of a typical pH measurement system. pH electrode 1 and reference electrode 3 are partially immersed in sample solution 5 in container 7 and both electrodes are electrically connected to electrometer 17 by conductors 13 and 15. The potential across a glass sensing-membrane 8 of the pH electrode changes in proportion to the difference in pH between external sample solution 5 and a pH buffer solution 9 contained within the sensor membrane. An electrochemical half-cell 11 is used to establish a stable electrical connection between the inner buffer solution 9 and the wire conductor 13 leading to the electrometer. This half-cell has a fixed potential usually determined by the anion concentration of the buffer solution. The difference in potential between the external solution 5 and the positive electrometer terminal changes with pH, and it is this change in potential that is to be monitored. The role of the reference electrode is to establish a fixed half-cell potential between the external measured solution and the negative electrometer terminal. In measurements of unknown solutions, the half-cell cannot be directly immersed in the sample, since its potential will vary with the unknown anionic activity of the solution. Therefore, an indirect reference connection is made by immersing the reference half-cell electrode 2 into a known electrolyte 19 and then establishing electrical contact between this electrolyte and the measured solution through a reference junction 21 positioned in outlet 23 of the electrode envelope. The reference junction usually consists of a porous ceramic plug, asbestos fiber, or other means of achieving a fluid mechanical leak. The reference junction functions primarily as a flow restrictor and filtration member, and also serves to define the shape of the interface between the solutions. Ideally, the junction is sufficiently porous to allow a low resistance contact, preferably well below 10 Kohm, but is not so porous that the solutions become mutually contaminated. As already indicated and by way of illustration only, the half-cell electrode and half-cell electrolyte of the reference electrode typically are silver-silver chloride and AgCl-saturated 4 M KCl, respectively. Similarly, the half-cell electrode and half-cell electrolyte of a typical pH electrode are silver-silver chloride and chloride-containing buffer, respectively.

Figure 2:
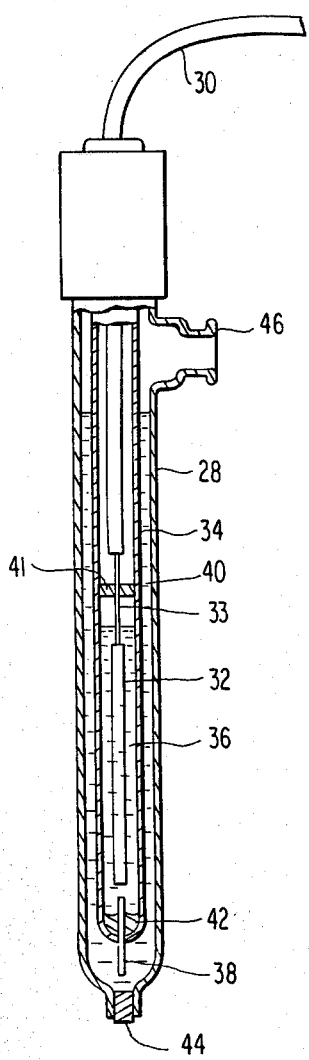
FIG. 2 of the Drawing depicts in cross section a reference electrode of the present invention.

FIG. 2 of the Drawing depicts in cross section a double junction reference electrode 28 of the present invention.

Electrical connection from an electrometer (not shown) to the half-cell electrode 32, positioned in housing 34, is by means of an insulated electrical conductor 30 and wire 33. Half-cell electrolyte 36 surrounds the half-cell electrode, both positioned beneath partition 41. Half-cell (inner) junction 38, the microporous barrier of the present invention, allows communication between the half-cell electrolyte and junction electrolyte 40, and is positioned in sealant 42, such as Hardman wet-patching epoxy. The junction electrolyte can be added through inlet 46 and can flow through reference (or outer) junction 44 into a sample solution, not shown. The microporous barrier extends into both the half-cell electrolyte and the junction electrolyte beyond both sides of the sealant.

Figure 3:
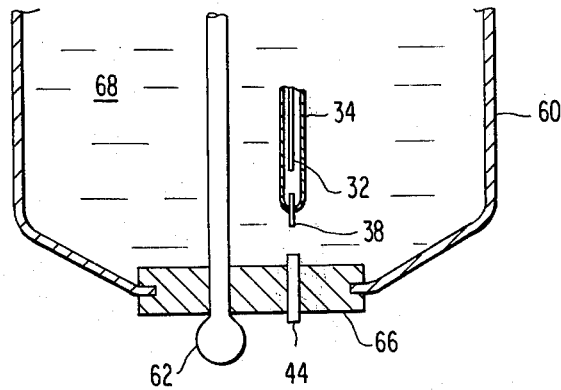
FIG. 3 of the Drawing depicts in partial cross section a combination electrode of the present invention.

FIG. 3 is a cross section of the lower end of a combination electrode 60 where both glass electrode 62 and reference junction 44 extend through grommet 66. The numerical designations for half-cell housing 34 and other reference electrode parts are as in FIG. 2. Reference junction electrolyte 68 is contained by the outer housing of the electrode.

In FIGS. 2 and 3, the microporous barrier 38 serves to limit the rate of solute transport between half-cell and junction electrolytes while allowing ionic electrical conduction. In the present invention, the inner (half-cell) junction is characterized by two transport parameters, flow permeability and electrical conductivity, which are inversely related to the ability of the junction to function as an effective barrier to electrolyte exchange. Flow permeability determines the rate of fluid flow through the junction in response to pressure differences across the junction, such pressure differences being caused primarily by changes in ambient temperature and pressure. Electrical conductivity determines the rate of diffusional transport across the junction in response to concentration differences across the junction, such concentration differences being caused primarily by use of different half-cell and junction electrolytes, electrolyte evaporation, etc. Both transport parameters are measured under defined test conditions, described hereinafter.

From a theoretical standpoint, the reason for defining diffusional transport in terms of conductance or reciprocal of resistance is set forth below, which is based on my finding that the diffusional exchange of an electrolyte through a porous barrier is directly proportional to the electrolytic conductance of the barrier when saturated with the same electrolyte and is independent of the barrier's size, shape or structural detail. This follows from the fact that steady-state ionic diffusion due to gradients of concentration and steady-state ionic conduction due to gradients of electric potential are governed by exactly the same differential equations and boundary conditions. Thus, the effectiveness of a diffusion barrier is completely characterized by its electrical resistance. The diffusional exchange across a barrier can be expressed in terms of an equivalent exchange of bulk volumes, for which I have derived the following theoretical expression:

$$\frac{dV}{dt} = \frac{R_o T}{2F2} \cdot \frac{1}{RC}$$

where $dV/dt$ is the equivalent volume exchange per unit time, $R_o$ is the universal gas constant, T is the absolute temperature, F is the Faraday constant, and R is the electrical resistance of the barrier when saturated with a monovalent (1-1) test electrolyte at concentration C. For a given electrolyte and barrier, the product RC is essentially constant.

Assuming T=25° C.=298° K. and C=4 M, we obtain $$\frac{dV}{dt} = \frac{0.12/\text{ohm-ml/hr}}{R}$$

$$= \frac{1050/\text{ohm-ml/yr}}{R}$$

Since most small ions have fairly similar mobilities, diffusional transport predictions based on barrier resistance in 4 M KCl should apply with fair accuracy to other small ions, in particular, to the heavy metal ions of the half-cell.

For a given porous barrier material, the electrical resistance and flow resistance of the barrier are affected equally by changes in its dimensions (e.g., thickness). But since diffusional transport of the barrier cannot be decreased without a corresponding, undesirable increase in barrier resistance, while flow transport can in principle be made as small as desired by increasing the fineness of the pore structure of the barrier material, the maximal blocking per given resistance of the barrier is achieved when flow transport is made negligible compared to diffusional transport. Resistance minimization is essentially achieved when typical flow transport is less than 10% of diffusional transport; for practical purposes, the diffusion-limited transport condition and its advantages persist as long as flow transport (dVf/dt)

does not exceed diffusional transport (dV$_d$/dt), which corresponds to the condition $$\frac{dV}{dt} f (@ \text{ 1 cm } Hg) < \frac{dV}{dt} d = \frac{0.12 \text{ ohm-ml/hr}}{R}$$

which implies $$R \cdot \frac{dV}{dt} f < 0.12 \text{ ohm} \cdot \text{ml} \cdot \text{hr}^{-1}$$

Thus, the microporous barrier of the present invention is such that when it is saturated with 4 M KCl, the product of the flow rate through the barrier at 1 cm Hg pressure multiplied by the electrical resistance of the barrier does not exceed 0.12 ohm-ml/hr. This product depends only on the material characteristics of the barrier, and not on its size or shape.

Expressed in terms of the electrical conductance of the junction, S=1/R, this condition becomes $$\frac{dV}{dt} /S < 0.12 \text{ ml} \cdot \text{hr}^{-1} \cdot \text{mho}^{-1}$$

where mho is the unit of conductance which is equal to the reciprocal of the ohm.

As a practical matter, the ratio of the electrical conductance (inverse resistance) of the microporous barrier when saturated with 4 M KCl divided by the volume of junction electrolyte contained by the electrode, is desired to be below $10^{-4}$ mho/ml. This limits the level of diffusional contamination of junction electrolyte by half-cell electrolyte to below 10% per year.

For example, the volume of junction electrolyte in a typical double junction reference electrode is 3 ml. Assuming we wish to keep diffusional contamination of this electrolyte below 4 percent at the end of one year, the required barrier resistance is $$R = \frac{1 \text{ year}}{(.04)3\text{ml}} \times (0.12 \text{ ml} \cdot \text{ohm} \cdot \text{hr}^{-1}) = \text{about } 8000$$

ohms, a fairly high resistance.

8000 ohms corresponds to $1.25 \times 10^{-4}$ mhos per 3 ml junction electrolyte, or about $0.4 \times 10^{-4}$ mhos per ml of junction electrolyte.

Similarly, the flow permeability of the microporous barrier to aqueous 4 M KCl solution under 1 cm Hg pressure desirably is less than 0.1 milliliter per year, per milliliter of junction electrolyte in the reference electrode. One cm Hg pressure represents the average effective magnitude of atmospheric pressure fluctuations which serve to drive electrolyte flow through the barrier; thus, under this condition, contamination of junction electrolyte by flow of half-cell electrolyte is typically below 10% per year.

Based on practical considerations, then, the flow transport of the barrier desirably is less than 0.05, preferably less than 0.01, ml per year per ml of junction electrolyte, and the electrical conductance of the barrier desirably is about 0.1 to $0.8 \times 10^{-4}$ mho, preferably about 0.2 to $0.6 \times 10^{-4}$ mho, per ml of junction electrolyte.

In an exemplified embodiment, using a rod of porous VYCOR ® glass manufactured by Corning Glass Works, flow transport at 1 cm Hg is about 0.5% of diffusional transport. Also, the resistivity of porous VYCOR ® when saturated with 4 M KCl is such that a section of VYCOR ® rod 0.6 mm in diameter and 8 mm in length will have a resistance of approximately 8 kilo-ohms, equivalent to a conductance of $0.4 \times 10^{-4}$ mho/ml for an electrode with 3 ml of junction electrolyte. Porous VYCOR ® is an open network, microporous glass of 96 percent silica formed by phase separation and leaching of a parent glass to yield about 50 percent porosity and about 70 Å mean pore size. Pore size can vary widely, with at least mean pore sizes of 40 to roughly 1000 Å being usable. Other open porous materials, such as porous sintered ceramics, for example, sintered titania or zirconia, or porous organic membranes, for example, crosslinked polyvinylalcohol, could be used in place of the porous glass. However, a particular advantage of using porous VYCOR ® in the present invention is that it has low surface charge, so that there is very little offset and drift in potential due to barrier space charge when the electrode is filled with junction electrolytes of low ionic strength.

A primary advantage of the present electrode is the fast and accurate electrode response made possible by the use of 4 M KCl junction electrolyte which is kept pure for an extended time by a diffusion barrier of minimal resistance.

There are many additional advantages of the present invention, including the ability to use electrolytes of dissimilar ionic content (that is, for example, a nonchloride filling solution with Ag/AgCl half-cell), reduction of drift caused by diffusion of half-cell ions, exceptional stability in potential at elevated temperatures, elimination of thermal hysteresis, and so on.

The high resistance of the microporous barrier used in the present invention may increase the electrical noise several fold, but the additional noise can be suppressed by capacitatively coupling the two electrolytes to allow AC current to bypass the high resistance microporous barrier as disclosed in my co-pending application Ser. No. 230,457.

In order to determine whether a particular material can be used as the microporous barrier of the present invention, it is only necessary to fabricate a barrier, preferably in the size and configuration of use in the reference electrode, saturate it with 4 M KCl, and then measure the electrical resistance and flow permeability of the barrier. Resistance can be measured by applying a constant-current pulse through the barrier, and determining the resulting shift in voltage across the barrier by means of reference electrodes immersed on either side of the barrier. Flow rate can be determined by applying a positive pressure head across the barrier by means of a column of electrolyte and measuring the electrolyte expelled per unit time. A 12 cm head of 4 M KCl is equivalent to 1 cm Hg. Very low flow rates can be measured by applying large pressure heads and measuring the rate of flow of 4 M KCl into pure distilled water by means of an analytical technique which is very sensitive to KCl concentration, e.g., an ion-selective electrode for Cl$^-$. With microporous barriers of the present invention, it may be necessary to account for diffusional transport by pre-exposing the pressurized barrier to pure water to allow formation of a steady-state diffusional profile, and then determining the flow-transport component from the slope of a graphical plot of total transport versus applied pressure.

Variations of the present invention will be apparent to the skilled artisan. In particular, the use of 4 M KCl to determine barrier resistance as prescribed hereinbefore is only a test condition and, consequently, should not be construed as limiting either the spirit or the scope of the present invention. Thus, other compositions and concentrations of half-cell and junction electrolytes can be used freely in the double junction reference electrodes of the present invention. It should be noted, however, that the electrical resistance properties of the microporous barrier employed in the present invention when actually saturated with electrolytes other than 4 M KCl may differ significantly from the values obtained when saturated with 4 M KCl.

What is claimed is:

1. In a double junction electrode comprising
   (a) a first housing containing an electrochemical half-cell being electrically connectable to an external measuring means and consisting essentially of a half-cell electrode and a half-cell electrolyte,
   (b) a second housing containing a junction electrolyte,
   (c) a half-cell junction allowing ionic conduction between said half-cell electrolyte and said junction electrolyte, and
   (d) a reference junction allowing ionic conduction between said junction electrolyte and an external sample to be measured, the improvement which comprises said half-cell junction comprising a microporous barrier material having a structure of sufficiently fine pore size such that exchange between half-cell and junction electrolytes is limited by diffusion, rather than by flow, characterized in that, when said half-cell junction is saturated with 4 M KCl, the mathematical quotient of the liquid flow rate through said half-cell junction at 1 cm Hg pressure divided by the ionic electrical conductance of said half-cell junction is less than about $0.12$ ml.hr$^{-1}$.mho$^{-1}$.

2. The reference electrode of claim 1 wherein said mathematical quotient is less than about $0.012$ ml.hr$^{-1}$.mho$^{-1}$.

3. The reference electrode of claim 1 or 2, wherein the microporous barrier is microporous glass, porous sintered ceramic, or porous organic membrane.

4. The reference electrode of claim 3, wherein the microporous barrier is microporous glass.

5. The reference electrode of claim 1, 2, or 4, wherein the half-cell electrode is silver-silver chloride.

6. The reference electrode of claim 5, wherein the half-cell and junction electrolytes consist essentially of AgCl-saturated KCl.

7. The reference electrode of claim 3, wherein the half-cell electrode is silver-silver chloride.

8. The reference electrode of claim 6, wherein the half-cell and junction electrolytes consist essentially of AgCl-saturated KCl.

* * * * *